US00PP16367P2

(12) United States Plant Patent
Bottoms

(10) Patent No.: US PP16,367 P2
(45) Date of Patent: Mar. 21, 2006

(54) ***SCHEFFLERA* PLANT NAMED 'NORMA JEAN'**

(50) Latin Name: *Schefflera arboricola*
Varietal Denomination: Norma Jean

(76) Inventor: Ellsworth D. Bottoms, 2518 Haas Road, Apopka, FL (US) 32712

( * ) Notice: Subject to any disclaimer, the term of this patent is extended or adjusted under 35 U.S.C. 154(b) by 51 days.

(21) Appl. No.: 11/022,061

(22) Filed: Dec. 24, 2004

(51) Int. Cl.
*A01H 5/00* (2006.01)

(52) U.S. Cl. ..... Plt./377
(58) Field of Classification Search ..... Plt./377
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Schefflera* plant named 'Norma Jean', characterized by its upright, outwardly spreading and mounded plant habit; short internodes; dense and bushy growth habit; broadly elliptic-shaped leaves; developing leaves with green and yellow green-colored variegation; and fully expanded leaves with darker green and light yellow green-colored variegation.

1 Drawing Sheet

Botanical designation: *Schefflera arboricola.*
Cultivar denomination: 'Norma Jean'.

BACKGROUND OF THE INVENTION

The present Invention relates to a new and distinct cultivar of *Schefflera* plant, botanically known as *Schefflera arboricola,* and hereinafter referred to by the cultivar name 'Norma Jean'.

The new *Schefflera* was discovered in May, 2001 by the Inventor in a controlled environment in Apopka, Fla., as a naturally-occurring branch mutation of the *Schefflera arboricola* cultivar Hong Kong, not patented. The new *Schefflera* was selected from within a population of plants of 'Hong Kong' and was selected on the basis of its unique foliage variegation.

Asexual reproduction of the new cultivar by cuttings in Apopka, Fla., since May, 2001, has shown that the unique features of this new *Schefflera* are stable and reproduced true to type in successive generations.

SUMMARY OF THE INVENTION

Plants of the cultivar Norma Jean have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Norma Jean'. These characteristics in combination distinguish 'Norma Jean' as a new and distinct cultivar of *Schefflera:*

1. Upright, outwardly spreading and mounded plant habit.
2. Short internodes; dense and bushy growth habit.
3. Broadly elliptic-shaped leaves.
4. Developing leaves with green and yellow green-colored variegation.
5. Fully expanded leaves with darker green and light yellow green-colored variegation.

Plants of the new *Schefflera* are similar to plants of the parent, the cultivar Hong Kong, in plant and growth habit, however plants of the new *Schefflera* differ primarily from plants of the cultivar Hong Kong in foliage variegation coloration.

Plants of the new *Schefflera* can be compared to plants of the cultivar PVN III, disclosed in U.S. Plant Pat. No. 14,541. However, in side-by-side comparisons conducted by the Inventor in Apopka, Fla., plants of the new *Schefflera* differed from plants of the cultivar PVN III in the following characteristics:

1. Plants of the new *Schefflera* had broader leaves than plants of the cultivar PVN III.
2. Plants of the new *Schefflera* had dark green and light yellow green-colored variegated foliage whereas plants of the cultivar PVN III had dark green and creamy white variegated foliage.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Schefflera.* The photograph comprises a side perspective view of a typical container of 'Norma Jean' with four plants per container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and the following description were grown with four plants per container and in a polypropylene-covered shadehouse in Apopka, Fla., that provided a 72% reduction of the ambient light level. During the production of the plants, day temperatures ranged from 70 to 90° F. and night temperatures ranged from 45 to 70° F. Plants were about one year old when the photograph and description were taken. Plants were not pinched.

Botanical classification: *Schefflera arboricola* cultivar Norma Jean.

Parentage: Naturally-occurring branch mutation of *Schefflera arboricola* cultivar Hong Kong, not patented.

Propagation:

*Type.*—By cuttings.

*Time to initiate roots, summer.*—About 30 days at 80 to 90° F.

*Time to initiate roots, winter.*—About 50 to 60 days at 50 to 60° F.

*Root description.*—Numerous, dense, freely-branching; fibrous; white in color.

Plant description:

*Form.*—Upright, outwardly spreading and mounded plant habit; inverted triangle; symmetrical. Short internodes; dense and bushy growth habit.

*Plant height.*—About 42 cm.

*Plant diameter.*—About 62 cm.

*Vigor.*—Moderately vigorous.

*Stem description.*—Length: About 32.5 cm. Diameter: About 1 cm. Internode length: Short, about 1.4 cm. Aspect: Upright to outwardly spreading. Strength: Flexible, but strong. Texture, young: Smooth, glabrous. Texture, mature: Woody. Color, young: Close to 146A. Color, mature: Close to 197C.

*Foliage description.*—Arrangement/appearance: Alternate; palmately compound with about seven to eight leaflets per leaf. Leaf diameter: About 14 cm by 16 cm. Leaflet length: About 8 cm. Leaflet width: About 4.2 cm. Leaflet shape: Broadly elliptic. Leaflet apex: Acute. Leaflet base: Attenuate. Leaflet margin: Entire. Leaflet texture, upper and lower surfaces: Smooth, glabrous; leathery. Leaflet luster, upper surface: Glossy. Leaflet luster, lower surface: Dull. Leaflet aspect: Slightly concave. Leaflet color: Developing foliage, upper surface: Random and irregularly shaped areas of close to 147A and close to 144A. Developing foliage, lower surface: Random and irregularly shaped areas of close to 191B and close to 146D. Fully expanded foliage, upper surface: Random and irregularly shaped areas of darker green than 147A and close to 154C. Fully expanded foliage, lower surface: Random and irregularly shaped areas of close to 147B and close to 146B to 146C. Veins, upper and lower surfaces: Similar to lamina. Leaflet petiole length: About 1.5 cm. Leaflet petiole diameter: About 2 mm. Leaflet petiole texture, upper and lower surfaces: Smooth, glabrous. Leaflet petiole color, upper and lower surfaces: Close to 144A to 146A. Leaf petiole length: About 10 cm. Leaf petiole diameter: About 2 mm. Leaf petiole texture, upper and lower surfaces: Smooth, glabrous. Leaf petiole color, upper and lower surfaces: Close to 146A to 147A.

Flower description: Flower development has not been observed on plants of the new *Schefflera*.

Disease/pest resistance: Plants of the new *Schefflera* have not been noted to be resistant to pathogens and pests common to *Schefflera*.

Weather tolerance: Plants of the new *Schefflera* have been observed to be tolerant to rain, wind and temperatures ranging from 32 to more than 100° F.

It is claimed:

1. A new and distinct cultivar of *Schefflera* plant named 'Norma Jean', as illustrated and described.

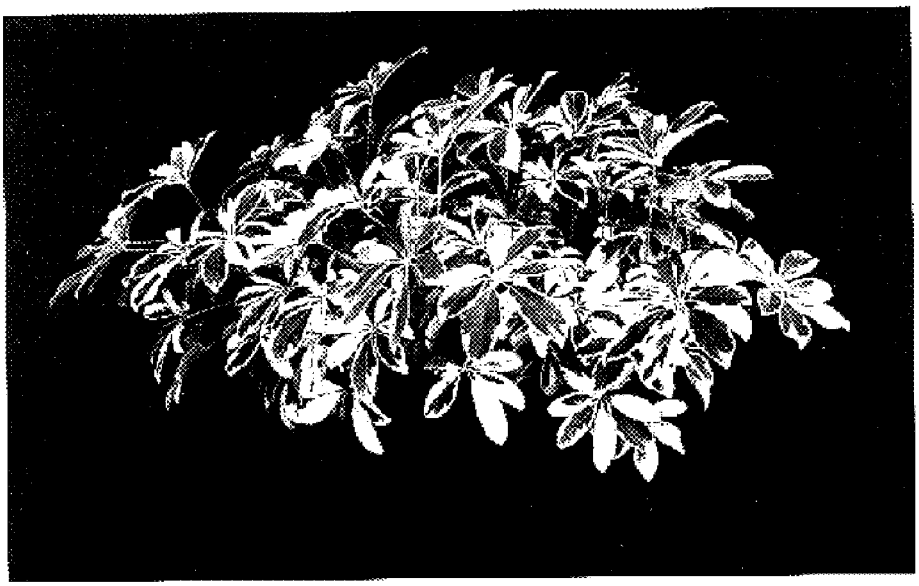

* * * * *